United States Patent [19]

Eckert et al.

[11] 4,263,313

[45] Apr. 21, 1981

[54] TOPICAL PHARMACEUTICAL FORMULATIONS, CARRIER COMPOSITIONS THEREFOR, AND PREPARATION THEREOF

[75] Inventors: Theodor Eckert; Fritz H. Kemper, both of Muenster; Martin Wischniewski, Neustadt a.Rbge.; Reinhard Hempel, Hanover, all of Fed. Rep. of Germany

[73] Assignee: Kali-Chemie Pharma GmbH, Hanover, Fed. Rep. of Germany

[21] Appl. No.: 880,155

[22] Filed: Feb. 22, 1978

[30] Foreign Application Priority Data

Feb. 24, 1977 [DE] Fed. Rep. of Germany ....... 2707878

[51] Int. Cl.$^3$ .................. A61K 31/40; A61K 31/195; A61K 31/415; A61K 47/00
[52] U.S. Cl. ............................. 424/273 P; 424/180; 424/230; 424/242; 424/274; 424/319; 424/365
[58] Field of Search ............................. 424/273 P, 365

[56] References Cited

U.S. PATENT DOCUMENTS 4,115,313  9/1978  Lyon et al. ........................... 424/365

FOREIGN PATENT DOCUMENTS 2357389  5/1974  Fed. Rep. of Germany.
1432784  4/1976  United Kingdom.

OTHER PUBLICATIONS

McCutcheon's Det. & Emulsifiers, 1970 Annual, p. 85.
Vogel et al., C.A. vol. 67 (1967) 89520y.
McCutcheon's Detergents & Emulsifiers, International Ed., 1976 Annual, pp. 23, 24, 25, 34 and 97.

*Primary Examiner*—Allen J. Robinson
*Attorney, Agent, or Firm*—Schwartz, Jeffery, Schwaab, Mack, Blumenthal & Koch P.C.

[57] ABSTRACT

A carrier composition for cutaneously absorbable topical pharmaceutical formulations of pharmacologically active agents is disclosed which comprises at least one partial glyceride of a fatty acid of medium chain length. This vehicle enhances the permeation of the topical formulation through the skin. A topical formulation which comprises this permeation enhancing vehicle is suitable for cutaneously applying pharmacologically active agents which are locally and/or systematically effective in the body.

8 Claims, No Drawings

TOPICAL PHARMACEUTICAL FORMULATIONS, CARRIER COMPOSITIONS THEREFOR, AND PREPARATION THEREOF

BACKGROUND OF THE INVENTION

The present invention relates to a permeability-enhancing carrier composition for topical pharmaceutical formulations and to topical pharmaceutical formulations which comprise a pharmacologically-active agent and the above carrier composition, and to methods for preparing such compositions and formulations.

It is well known in the art that the extent to which a topically-applied pharmacologically-active agent will penetrate into the skin and be further absorbed into the body is largely dependent on the type of carrier material, in the topical formulation, where it is applied and on the ability of this carrier material to penetrate into the skin. Triglycerides of fatty acids of medium or long chain length (chains containing about 6–18 carbon atoms) are known to enable pharmacologically-active agents to penetrate into the subepidermic layers of the skin. However, many pharmacologically-active agents are only poorly soluble in such triglycerides of fatty acids of medium or long chain length (about 6–18 carbon atoms), and because of this, their permeation into deeper layers of the skin takes place only to a limited degree and is slow and delayed. Further to the limited solubility of the pharmacologically-active agents in the triglycerides of fatty acids of medium or long chain length, the strong lipophilic properties of these triglyceride carrier materials also adversly affects the penetration into the skin of pharmacologically-active agents.

SUMMARY OF THE INVENTION

It is an object of the present invention to provide a vehicle composition for topical pharmaceutical formulations of pharmacologically-active agents, which improves the permeation of the pharmacologically-active agent through the skin into the body.

It is further object of the present invention to provide such a carrier composition which readily penetrates into the skin and which exhibits a sufficiently high dissolution capacity for pharmacologically-active agents to enhance the permeation of a pharmacologically-effective amount thereof through the skin and its absorption into the body.

It is a further object of the present invention to provide topical pharmaceutical formulations of pharmacologically-active agents which ensure a ready penetration from the site of application into the skin, preferably into the deeper layers thereof, and/or a permeation through the skin and absorption into the body system.

It is a further object of the present invention to provide such a topical formulation of primarily locally effective pharmacologically-active agents, such as anti-inflammatory agents, analgesics and antirheumatics, which provide for an increased speed and degree of permeation.

It is a further object of the present invention to provide such a topical formulation of primarily systemically-effective pharmacologically-active agents (which upon enteral application are largely normally destroyed in the gastric-intestinal tract and/or in the liver) which provide for a sufficiently high speed and the degree of permeation and absorption of these systemically-effective agents through the skin to permit a cutaneous application thereof.

In order to accomplish the foregoing objects according to the present invention, there is provided a pharmaceutical vehicle composition which is suitable for cutaneously-absorbable topical pharmaceutical formulations of pharmacologically-active agents and which comprises a carrier material comprising at least one partial glyceride of a fatty acid of medium chain length, preferably containing from about 6 to about 12 carbon atoms, and at least one pharmaceutical adjuvant.

Preferably the carrier composition further comprises a pharmaceutical additive having viscosity-improving gel-forming or structurizing properties and/or a free fatty acid of medium chain length.

According to the present invention, there is further provided a topical pharmaceutical formulation which is readily cutaneously absorbable and which comprises a pharmacologically-effective amount of at least one pharmacologically-active agent distributed in a vehicle comprising a permeation-enhancing amount of the above defined carrier composition.

According to the present invention there is further provided a method of medication which comprises cutaneously administering a pharmacologically-active agent to a larger mammal by applying a pharmacologically-effective amount of the above defined topical pharmaceutical formulation to its skin.

DETAILED DESCRIPTION OF THE INVENTION

Surprisingly it has been found that the penetration of pharmacologically-active agents into the skin and/or their permeation through the skin and their absorption into the body is considerably improved if they are applied cutaneously within a topical pharmaceutical formulation wherein the carrier material comprises mono- and diglycerides of fatty acids of medium chain length or mixtures thereof.

The high permeation rate of such a topical pharmaceutical composition is partially due to the fact that mono- and diglycerides of fatty acids of medium chain length possess excellent dissolving properties for dissolving hydrophilic as well as lipophylic pharmacologically-active agents. Furthermore, the mono- and diglycerides of fatty acids of medium chain length exhibit a more favorable balance between hydrophylic and lipophilic properties as compared with that of the triglycerides. Since the main transport mechanism for passing substances through the skin is that of a passive diffusion, this hydrophylic-lipophylic ratio enhances the permeation of the vehicle and the pharmacologically-active agents which are dissolved therein.

Partial glycerides of fatty acids of medium chain length comprise mono- and diglycerides of fatty acids, preferably saturated monocarboxylic acids having a chain length of preferably between about 6 and about 12, most preferably between about 8 and about 10 carbon atoms, and mixtures thereof. Especially suited are mono- and diglycerides of capric- and caprylic acid and mixtures thereof.

The term "pharmacologically-active agent" as used in the present specification and claims is meant to denote agents which are effective in larger mammals, in particular human beings, in treating or preventing diseases and/or disorders in the body functions and/or influencing the state of the body and its functions in a desirable manner. These pharmacologically-active agents include agents which exhibit a primarily local activity in the body near the site of their application as well as agents which exhibit a primarily systemic activity.

The vehicle composition according to the present invention is especially suited for preparing topical formulation of such pharmacologically-active agents which usually are applied cutaneously, yet which per se exhibit an unsatisfactorily slow and/or poor penetration into and/or permeation through the skin. This carrier composition is also suited for preparing topical formulations of such pharmacologically-active agents which possess a primarily systemic activity, yet which upon oral administration exhibit undesirable side effects in the gastro-intestinal tract and/or which are at least partially destroyed in the gastro-intestinal tract and/or are destroyed or inactivated in the liver immediately after their absorption from the gastro-intestinal tract. The present invention provides a possibility for cutaneously applying pharmacologically-active agents which previously could not be administered topically. Thus, the present invention provides a means for satisfying the need for protecting the pharmacologically-active agents from undesirable effects of the digestive secretions. Preparations according to the present invention are especially suited for cutaneously applying pharmacologically-active agents which possess anti-inflammatory, antirheumatic, analgesic, and/or antipyretic properties, whereby a high absorption rate through the skin is achieved. Examples of pharmacologically-active agents, which are advantageously applied in form of a topical formulation according to the present invention are flufenamic acid, escin, phenylbutazone (e.g. the commercial product Butazolidin, manufacturer Ciba-Geigy) indomethacin, diethyl aminosalicylate or progesterone.

The concentration of the pharmacologically-active agent in the topical formulations according to the present invention may vary considerably depending on the physical and chemical properties, especially the pharmacological activities of the agent, as well as on the amount of permeation enhancing partial glycerides present in the preparation and the treated condition and the therapy which is desired. Usually a satisfactory pharmacological result is obtained with topical formulations comprising from about 1 to about 10% by weight of the pharmacologically-active agent.

The topical formulations according to the present invention may take the form of compositions having a semisolid consistency, such as ointments, creams, jellies, foams, aerosols, or the like or the form of liquid solutions, suspensions, and emulsions.

Depending on the type of the pharmacological agent therein, the desired consistency and the contemplated mode of application, the carrier material in the vehicle composition according to the present composition may essentially consist of only the partial glycerides of fatty acids of medium chain length or may comprise additional carrier materials, such as pharmacologically-acceptable oils and water and/or such supplementary pharmaceutical adjuvants which are conventionally used in topical formulations, e.g., in conventional bases for ointments, creams, and jellies. In many cases it may be advisable to incorporate a structure-forming, thickening or gel-forming agent into the composition. Suitable such agents are, in particular, highly dispersed silicic acid (e.g., the commercial product "Aerosil"), bentonites, modified montmorillonites, such as alkyl ammonium salts of montmorillonites (e.g., the commercial products "Bentone"), wherein the alkylgroups may contain 1 to 20 carbon atoms, e.g., dimethyl-dialkyl-ammonium salts wherein the alkylgroups contain 16 to 18 carbon atoms, organic structure-forming, thickening and suspending agents, e.g., cetostearylic alcohol and modified castor oil products (e.g., the commercial product "Antisettle CVP"$^{(R)}$). Creams may be in the form of water-in-oil or oil-in-water emulsions which may contain conventional pharmaceutically-acceptable emulsifying agents.

In addition to the mono- and/or diglycerides of fatty acids of medium chain length and conventional pharmaceutical adjuvants, in particular structure-forming agents, the compositions may further comprise free fatty acids of medium chain length. These free acids serve to maintain the desirable acid-level of the skin. The free fatty acids of medium chain length preferably also contain from about 6 to about 12 carbon atoms. Capric- and caprylic acids are especially prefered since they are substantially odorless. The amount of free fatty acids in the composition may vary considerably depending on the chemical and physical properties of the other ingredients therein and preferably may be in the range of from about 5 to about 35% by weight.

The amount of absorption-enhancing partial glycerides of fatty acids of medium chain length in the vehicle composition according to the present invention may vary considerably depending on the physical and chemical properties of the pharmacologically-active agent for the formulation of which it is contemplated, as well as on the chemical and physical properties of any other ingredients of the compositions. Typically, satisfactory results are obtained with carrier compositions wherein the amount of partial glycerides of fatty acids of medium chain length is between about 20 and about 100%, preferably between about 40 and about 99% of the vehicle.

The ratio between the amounts of pharmacologically-active agent and of absorption-enhancing partial glycerides of fatty acids of medium chain length in the topical formulation according to the present invention may vary considerably depending on the physical and chemical properties of the agent, its pharmacological activity and the treated condition and the therapy which is desired, as well as on the properties of any other ingredients in the formulations. Usually, satisfactory results are obtained with topical formulation wherein the ratio between the amounts of the pharmacologically-active agent and the partial glycerides is from about 1:2 to about 1:100 preferably from about 1:5 to about 1:50.

Pharmaceutical adjuvants which may be comprised in the vehicle composition comprise adjuvants which are conventionally applied in the preparation of ointments, jellies, and lotions, for example thickening agents, emulsifying agents, antioxidents: hygroscopic agents, anti-molding agents, perfumes, and the like.

The vehicle compositions, according to the present invention are prepared in any conventional manner by homogenously mixing the various ingredients at a temperature which is sufficiently elevated so that the partial glycerides of the fatty acids of medium chain length are liquid, and subsequently allowing the resulting mixture to cool to room temperature.

The topical formulations according to the present invention are prepared in any conventional manner, e.g., either by dissolving the pharmacologically-active agents in the partial glycerides and optionally subsequently adding additional adjuvants to the mixture or by homogenously mixing or dissolving the pharmacologically-active agents with or in a previously prepared carrier composition comprising the partial glycerides and any optional additional adjuvants. Depending on the solubility and/or the dissolution rate of the pharmacologically-active agent in the carrier composition and the consistency of the composition at room temperature, the dissolving may be done at room temperature or under moderate heating.

The invention will now be further described by the following non-limitive examples which are intended to be illustrative only.

EXAMPLE 1

Escin containing topical gel formulation 2 g of escin are incorporated into 10 g of a mixture of mono- and diglycerides of fatty acids of medium chain length (commercial product "Witafrol"(R), manufacturer: Dynamit Nobel AG) under heating. A stable gel is obtained. This gel can be further diluted by adding further pharmaceutically-acceptable carriers and additives, e.g., triglycerides of fatty acids, in order to obtain a topical formulation wherein the concentration of escin is sufficient for providing a therapeutically-effective amount of escin per dosage unit.

EXAMPLE 2

Vehicle for topical gel formulations 0.6 g of highly dispersed silicic acid (commercial product "Aerosil"(R), manufacturer: Degussa) are incorporated into 10 g of a mixture of mono- and diglycerides of fatty acids of medium chain length (commercial product "Witafrol"(R), manufacturer: Dynamit Nobel, A.G.). A transparent gel is obtained.

EXAMPLE 3

Vehicle for topical cream formulations

An emulsion is prepared by mixing 15 g of an emulsifying cetostearylalcohol, 10 g of capric acid, 12 g of a mixture of mono- and diglycerides of fatty acids of medium chain length (commercial product "Witafrol"(R), manufacturer: Dynamit Nobel, A.G.), and 75 g of water. This emulsion is a vehicle for topical formulations which is especially suited for adjusting the natural acidic condition of the skin.

EXAMPLE 4

Vehicle for topical formulations 50 g of an organic ammonium salt of montmorillonite (commercial product "Bentone"(R), manufacturer: NL-Industries Inc., Hightstown) is incorporated into 50 g of a mixture of mono- and diglycerides of fatty acids of medium chain length (commercial product "Witafrol"(R), manufacturer: Dynamit Nobel, A.G.), under agitation.

EXAMPLE 5

Vehicle for topical formulations 20 g of an organic ammonium salt of montmorillonite (commercial product "Bentone"(R), manufacturer: NL-Industries Inc., Hightstown) are incorporated into a solution of 30 g of capric acid in 50 g of a mixture of mono- and diglycerides of fatty acids of medium chain length (commercial product "Witafrol"(R), manufacturer: Dynamit Nobel, A.G.) under agitation. The resulting mixture also is a vehicle for topical formulations which is suitable for adjusting the natural acidic condition of the skin.

EXAMPLE 6

Vehicle for topical gel formulations 25 g of benzylidene sorbitol are dissolved in 100 ml of dimethyl formamide under moderate heating. This solution is homogenously mixed with a 2125 g of a mixture of mono- and diglycerides of fatty acids of medium chain length (commercial product "Witafrol"(R), manufacturer: Dynamit Nobel, A.G.) and the resulting mixture is allowed to stand for several hours until a transparent gel is formed.

EXAMPLE 7

Flufenamic acid containing gel 30 g of flufenamic acid are dissolved in 970 g of the gel which is described in Example 6 under agitation and moderate heating. A transparent gel is obtained and no recrystallization of flufenamic acid therefrom is observed.

EXAMPLE 7a

An antiphlogistically effective amount of the gel which is prepared according to Example 7 is applied to the skin of an adult person twice a day for an antiphlogistic treatment. When the gel is applied to the skin, an extraordinarily fast absorption of the antiphlogistically active agent takes place.

EXAMPLE 8

Indomethacin containing gel

A solution of 50 g of indomethacin in 40 g of dimethylformamide is homogenously mixed with 910 g of the gel-base which is prepared according to Example 6, whereby a highly compatible indomethacin-formulation is obtained.

EXAMPLE 8a

An anti-rheumatically effective amount of the gel which is prepared according to Example 8 is applied to the skin of an adult person for an anti-rheumatic treatment. From this gel, indomethacin, which usually is only applied orally or rectally, is readily absorbed without causing any undesirable side effects.

EXAMPLE 9

Phenylbutazone containing gel

Analogously to the procedure described in Example 8, a gel containing 5% by weight of phenylbutazone is prepared.

EXAMPLE 10

Diethylaminosalicylate containing gel

Analogously to the procedure described in Example 7, a gel containing 10% by weight of diethylaminosalicylate is prepared. Such a high concentration can not be achieved in conventional lipophilic vehicles.

EXAMPLE 11

Vehicle for topical formulations 10 g of a modified castor oil product (commercial product "Antisettle CVP"(R), manufacturer: Cray Valley Products, London) are dissolved under agitation and moderate heating in 990 g of a mixture of monoand diglycerides of fatty acids of medium chain length (commercial product "Witafrol"(R), manufacturer: Dynamit Nobel, A.G.). A transparent gel is obtained into which lipoid-soluble pharmacologically-active agents can be incorporated.

The improved level of permeation and absorption of pharmacologically-active agents through the skin from topical formulations according to the present invention is demonstrated by determination of the level of the respective pharmacological agents in the blood or determination of the amount of pharmacologically active agent which is excreted through the kidneys.

A surface of about 12 cm×12 cm from the belly of female rabbits (species: White New Zealanders) having an average weight of about 3.3 kg is freed of hair. 18 hours before the beginning of the test, the animals are deprived of food. The animals are narcotized. Subsequently to applying a tracheal catheter, a plastic catheter is introduced into the arteria carotis and the bladder outlet is tied off in such a manner that the amount of urine which is excreted during the test period is collected in the bladder.

The depilated belly surface is cleaned by rubbing it with a 70% ethanol solution. After drying it, the test-solutions are uniformly distributed over the bare surface and are rubbed into the skin during a period of 3 minutes.

The test solutions are prepared by dissolving radioactively-labelled test substances, diethylaminosalicylate, indomethacin, progesterone, and phenylbutazone, in the following mixtures of mono- and diglycerides of capric and caprylic acids:

Witafrol 7420(R) (commercial product, manufacturer: Dynamit Nobel, A.G.)
WL 2391 (commercial product, manufacturer: Gattefosse)

Comparative solutions of the radioactive substances are prepared in the following solvents: diethyl aminosalicylate in water, indomethacin in polyethylene glycol 400 (commercial product Lutrol, manufacturer: BASF), progesterone in ethanol, and phenylbutazone in diethylene glycol mono-ethyl ether (commercial product Transcutol, manufacturer: Gattefosse SA). These comparative solutions are applied to the rabbits in the same manner as the above test solutions.

For determining the blood level values, 0.6 ml samples of blood are taken at 1 hour intervals (the last sample is taken after 10 hours). For determining the radioactivity in the urine, the urine is recovered at the end of the test period after 10 hours by puncture of the bladder. The radioactivity is determined in aliquot portions of the blood samples and the urine samples in the conventional manner.

The values which are determined at the end of the test period after 10 hours are shown in the table below. The data in the table denote the amounts of the pharmacologically-active agent which is found in the blood and the urine in % of the applied dose of the agent.

TABLE

AMOUNT OF PHARMACOLOGICALLY-ACTIVE AGENT WHICH IS DETERMINED IN THE URINE AND THE BLOOD 10 HOURS AFTER APPLYING THE TOPICAL FORMULATION (% OF THE ADMINISTERED DOSE)

| | % Diethyl aminosalicylate | | % Indomethacin[3] | | % Progesterone[4] | | % Phenylbutazone | |
|---|---|---|---|---|---|---|---|---|
| | Blood | Urine | Blood | Urine | Blood | Urine | Blood | Urine |
| Solution Comparative | 0.17[1] | 0.6[1] | 0.04 | 0.03 | 0.07 | 0.6 | 0.37[5] | 0.46[5] |
| Solution in Witrafol 7420 | 2.96[2] | 4.2[2] | 0.18 | 2.5 | | | 0.52[6] | 0.51[6] |
| Solution in WL 2391 | 2.59[2] | 5.3[2] | 0.14 | 2.8 | 0.19 | 2.3 | | |
| | 4.48[1] | 10.3[1] | | | | | | |

Administered dose:
[1] 1 mg/kg in 1 ml of the solvent
[2] 1 mg/kg in 6 ml of the solvent
[3] 5 mg/kg in 4 ml of the solvent
[4] 20 mg/kg in 1 ml of the solvent
[5] 50 mg/kg in 2 ml of the solvent
[6] 50 mg/kg in 4 ml of the solvent

What is claimed is:

1. In a topical pharmaceutical composition including a pharmacologically-effective amount of a pharmacologically-active agent distributed in a vehicle suitable for topical application to human and animal skin, wherein the pharmacologically-active agent comprises phenylbutazone, the improvement comprising said vehicle consisting essentially of an active-ingredient-absorption-enhancing amount of from about 20 to 100% by weight of a partial glyceride of a fatty acid of medium chain length selected from a monoglyceride or a diglyceride of a fatty acid containing from about 6 to about 12 carbon atoms or a mixture thereof, and from about 0 to 80% of one or more pharmaceutical adjuvants, whereby enhanced absorption of the active agent results upon application of the composition to the skin.

2. A topical composition as defined in claim 1, wherein the vehicle comprises from about 40 to 100% of the partial glyceride of a fatty acid of medium chain length.

3. A topical composition as defined in claim 1, wherein the amount of the pharmacologically-active agent is from about 1 to about 10% by weight of the total composition.

4. A topical composition as defined in claim 1, wherein the weight ratio of pharmacologically-active agent to partial glyceride of a fatty acid is from about 1:5 to about 1:50.

5. A method of enhancing the penetration through human and animal skin of a pharmacologically active agent comprising phenylbutazone and being capable of eliciting a physiological effect upon topical application thereof, which comprises the step of concurrently topically administering to the skin an amount of said active agent effective to produce the desired physiological effect and an amount of a vehicle consisting essentially of from about 20 to 100% by weight of a partial glyceride of a fatty acid of medium chain length selected from a monoglyceride or a diglyceride of a fatty acid containing from about 6 to about 12 carbon atoms or a mixture thereof, and from about 0 to 80% by weight of one or more pharmaceutical adjuvants, sufficient to effectively enhance penetration of said active agent to achieve the desired physiological result.

6. A method according to claim 5, wherein the vehicle comprises from about 40 to 100% of the partial glyceride of a fatty acid of medium chain length.

7. A method according to claim 5, wherein the amount of the pharmacologically-active agent is from about 1 to 10% by weight of the total composition.

8. A method according to claim 5, wherein the weight ratio of pharmacologically-active agent to partial glyceride of a fatty acid is from about 1:5 to about 1:50.

* * * * *